US012633411B2

(12) United States Patent
Siewerdsen et al.

(10) Patent No.: US 12,633,411 B2
(45) Date of Patent: May 19, 2026

(54) DATA ANALYTICS FOR PREDICTIVE MODELING OF SURGICAL OUTCOMES

(71) Applicant: The Johns Hopkins University, Baltimore, MD (US)

(72) Inventors: Jeffrey H. Siewerdsen, Baltimore, MD (US); Nicholas Theodore, Ruxton, MD (US); Tharindu De Silva, Baltimore, MD (US); Satyanarayana S. Vedula, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 583 days.

(21) Appl. No.: 17/310,933

(22) PCT Filed: Feb. 26, 2020

(86) PCT No.: PCT/US2020/019946

§ 371 (c)(1),
(2) Date: Aug. 31, 2021

(87) PCT Pub. No.: WO2020/180566

PCT Pub. Date: Sep. 10, 2020

(65) Prior Publication Data

US 2022/0157459 A1 May 19, 2022

Related U.S. Application Data

(60) Provisional application No. 62/812,691, filed on Mar. 1, 2019.

(51) Int. Cl.
| | |
|---|---|
| *G16H 50/20* | (2018.01) |
| *G16H 20/40* | (2018.01) |
| *G16H 30/40* | (2018.01) |

(52) U.S. Cl.
CPC ............. *G16H 50/20* (2018.01); *G16H 20/40* (2018.01); *G16H 30/40* (2018.01)

(58) Field of Classification Search
CPC ........ G16H 50/20; G16H 20/40; G16H 30/40; G16H 50/70; G06N 7/01; G06N 3/08; G06N 5/01; G06N 20/10; G06N 20/20
See application file for complete search history.

(56) References Cited

U.S. PATENT DOCUMENTS

| | | | |
|---|---|---|---|
| 9,547,940 B1 | 1/2017 | Sun et al. | |
| 9,646,423 B1 | 5/2017 | Sun et al. | |

(Continued)

OTHER PUBLICATIONS

Extended European Search Report for Application No. EP20765793.3, mailed on Oct. 21, 2022, 9 pages.

(Continued)

*Primary Examiner* — Peter H Choi
(74) *Attorney, Agent, or Firm* — Harrity & Harrity, LLP

(57) ABSTRACT

A device may receive a set of perioperative images including a set of pre-operative images depicting one or more anatomical structures of a surgical candidate. The set of pre-operative images may be processed using image analysis techniques to determine a first set of quantitative measures related to the anatomical structure(s) of the surgical candidate. The device may use a data model that has been trained based on perioperative data associated with a patient cohort sharing clinical characteristics with the surgical candidate to predict outcomes from one or more therapeutic options for the surgical candidate based on the first set of quantitative measures and a second set of quantitative measures related to a profile associated with the surgical candidate. Based on the predicted outcomes, the device may provide, to a client device, a recommendation relating to the therapeutic options for the surgical candidate and information to support the recommendation.

20 Claims, 9 Drawing Sheets

(56)                References Cited

U.S. PATENT DOCUMENTS

| | | | |
|---|---|---|---|
| 9,788,786 | B2 | 10/2017 | Pfrengle et al. |
| 11,278,413 | B1 * | 3/2022 | Lang ..................... G16H 50/50 |
| 2017/0319165 | A1 | 11/2017 | Averbuch |
| 2017/0340755 | A1 | 11/2017 | Maiocchi et al. |
| 2018/0344308 | A1 * | 12/2018 | Nawana ................. A61B 34/25 |
| 2020/0268457 | A1 * | 8/2020 | Wolf ............. G06Q 10/063112 |

OTHER PUBLICATIONS

International Search Report and Written Opinion for Application No. PCT/US2020/019946, mailed on Jun. 11, 2020, 7 pages.

International Search Report and Written Opinion—PCT/US2020/019946—ISA/RU—Jun. 11, 2020.

De Silva et al., "3D-2D image registration for target localization in spine surgery: investigation of similarity metrics providing robustness to content mismatch," Physics in Medicine & Biology, Apr. 21, 2016, vol. 61, No. 8, pp. 3009-3025.

Otake et al., "3D-2D registration in mobile radiographs: algorithm development and preliminary clinical evaluation," Physics in Medicine & Biology, 2015, vol. 60, No. 5, pp. 2075-2090.

Staartjes et al., "Deep learning-based preoperative predictive analytics for patient-reported outcomes following umbar diskectomy: feasibility of center-specific modeling," The Spine Journal, Nov. 16, 2018, vol. 19, Issue 5, 9 pages.

Khor et al., "Development and Validation of a Prediction Model for Pain and Functional Outcomes After Lumbar Spine Surgery," JAMA Surgery, Mar. 7, 2018, vol. 153, Issue 7, pp. 634-642.

Steinmetz et al., "Value of Adding Predictive Clinical Decision Tools to Spine Surgery," JAMA Surgery, Jul. 2018, vol. 153, Issue 7, p. 643.

Dietz et al., "Variability in the utility of predictive models in predicting patient reported outcomes following spine surgery for degenerative conditions: a systematic review," Neurosurgical Focus, Nov. 2018, vol. 45, Issue 5, 9 pages.

Brusko et al., "Machine-Learning Models: The Future of Predictive Analytics in Neurosurgery," Neurosurgery, Jul. 2018, vol. 83, Issue 1, pp. E3-E4.

Spratt et al., "A predictive model for outcome after conservative decompression surgery for lumbar spinal stenosis," European Spine Journal, Feb. 2004, vol. 13, No. 1, 8 pages.

Försth et al., "A Randomized, Controlled Trial of Fusion Surgery for Lumbar Spinal Stenosis," The New England Journal of Medicine, Apr. 14, 2016, vol. 374, No. 15, pp. 1413-1423.

Desai et al., "Outcome Variation Across Centers After Surgery for Lumbar Stenosis and Degenerative Spondylolisthesis: The SPORT Experience," Spine, Apr. 15, 2013, vol. 38, Issue 8, pp. 678-691.

Kao et al., "Short-term and long-term revision rates after lumbar spine discectomy versus laminectomy: a population-based cohort study," BMJ Open, 2018, vol. 8, No. 7, 10 pages.

Baber et al., "Failed back surgery syndrome: current perspectives," Journal of Pain Research, 2016, vol. 9, pp. 979-987.

Drazin et al., "Treatment of Recurrent Disc Herniation: A Systematic Review," Cureus, May 23, 2016, vol. 8, No. 5, 12 pages.

Fritzell et al., "2001 Volvo Award Winner in Clinical Studies: Lumbar Fusion Versus Nonsurgical Treatment for Chronic Low Back Pain," Spine, 2001, vol. 26, No. 23, pp. 2521-2534.

Ghogawala et al., "Laminectomy plus Fusion versus Laminectomy Alone for Lumbar Spondylolisthesis," The New England Journal of Medicine, Apr. 14, 2016, vol. 374, No. 15, pp. 1424-1434.

Christensen, "Lumbar spinal fusion. Outcome in relation to surgical methods, choice of implant and postoperative rehabilitation," ACTA Orthopaedica Scandinavica Supplementum 2004, vol. 75, No. 313, 48 pages.

Patnaik, "Imaging features of primary tumors of the spine: A pictorial essay," Indian Journal of Radiology and Imaging, May 2016, vol. 26, No. 2, pp. 279-289.

Zhang et al., "Magnetic Resonance T2 Image Signal Intensity Ratio and Clinical Manifestation Predict Prognosis After Surgical Intervention for Cervical Spondylotic Myelopathy," Spine, 2010, vol. 35, No. 10, 4 pages.

Tetreault et al., "The modified Japanese Orthopaedic Association scale: establishing criteria for mild, moderate and severe impairment in patients with degenerative cervical myelopathy," European Spine Journal, Jan. 2017, vol. 26, No. 1, pp. 78-84.

Revanappa et al., "Comparison of Nurick grading system and modified Japanese Orthopaedic Association scoring system in evaluation of patients with cervical spondylotic myelopathy," European Spine Journal, Sep. 2011, vol. 20, No. 9, pp. 1545-1551.

* cited by examiner

100

125

Extract, from pre-operative images, patient-specific image analytic features

130

Use data model to determine therapeutic pathway and/or select surgical parameters based on patient-specific image analytic features

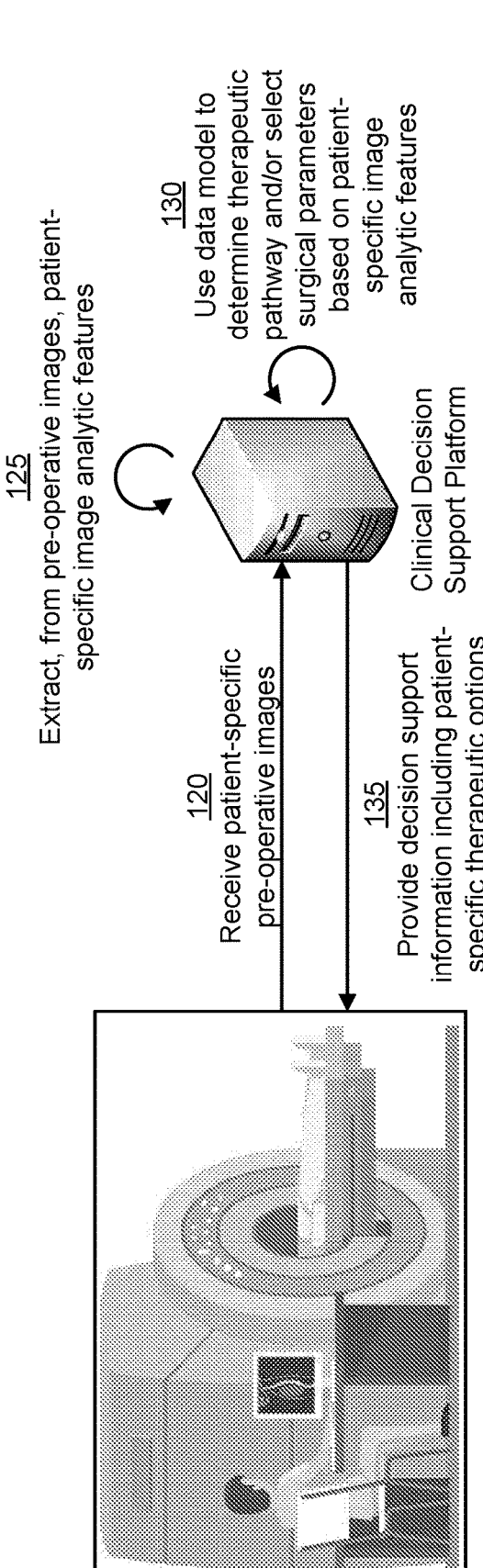

Clinical Decision Support Platform

120

Receive patient-specific pre-operative images

135

Provide decision support information including patient-specific therapeutic options

145
Receive patient-specific
post-operative data

140
Receive patient-specific
intra-operative images

Data Storage
Device

Clinical Decision
Support Platform

150
Use data model to
predict surgical outcome
and/or determine
rehabilitative pathway
based on patient-specific
perioperative data

400

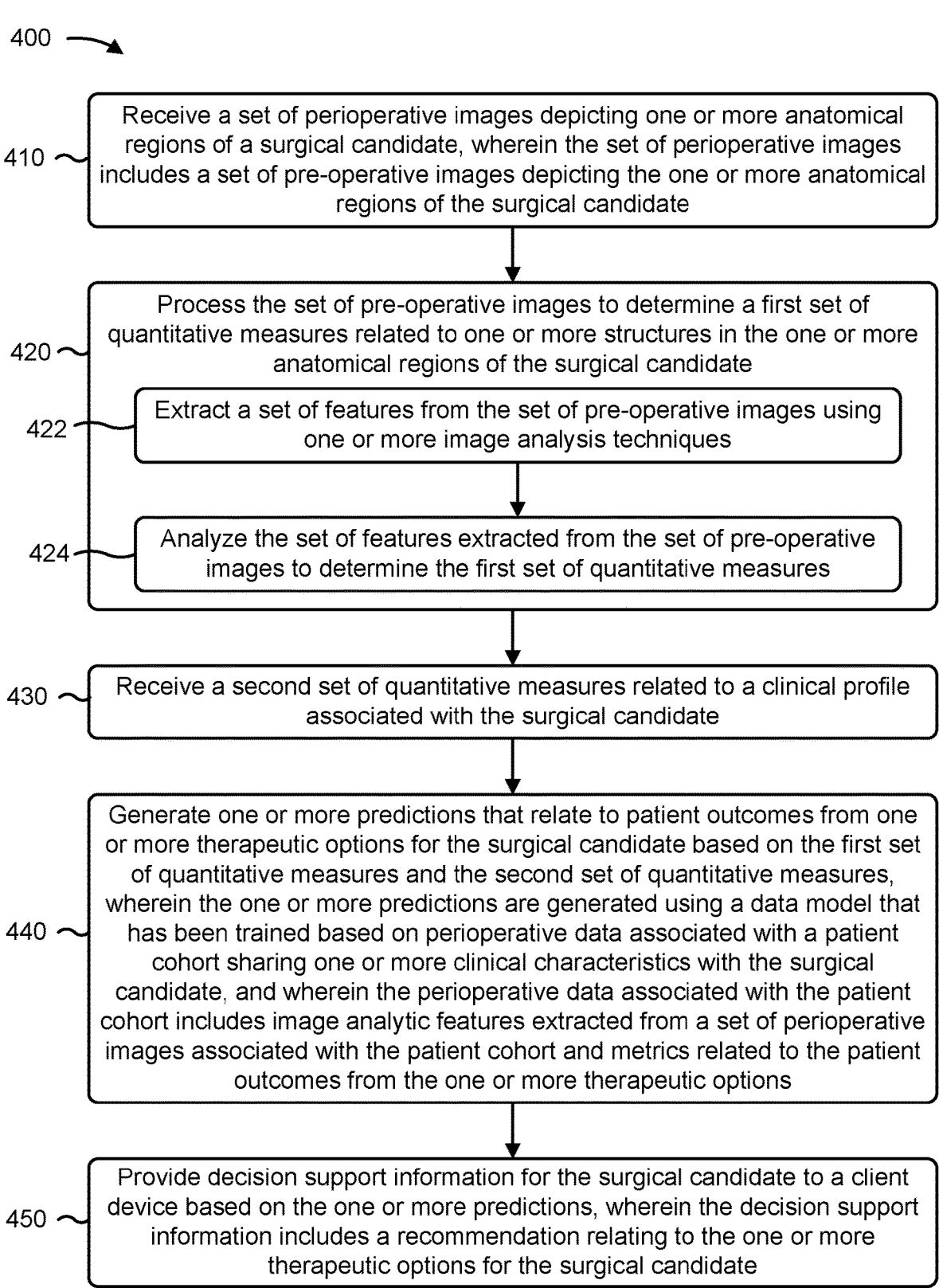

410
Receive a set of perioperative images depicting one or more anatomical regions of a surgical candidate, wherein the set of perioperative images includes a set of pre-operative images depicting the one or more anatomical regions of the surgical candidate 420
Process the set of pre-operative images to determine a first set of quantitative measures related to one or more structures in the one or more anatomical regions of the surgical candidate 422
Extract a set of features from the set of pre-operative images using one or more image analysis techniques 424
Analyze the set of features extracted from the set of pre-operative images to determine the first set of quantitative measures 430
Receive a second set of quantitative measures related to a clinical profile associated with the surgical candidate 440
Generate one or more predictions that relate to patient outcomes from one or more therapeutic options for the surgical candidate based on the first set of quantitative measures and the second set of quantitative measures, wherein the one or more predictions are generated using a data model that has been trained based on perioperative data associated with a patient cohort sharing one or more clinical characteristics with the surgical candidate, and wherein the perioperative data associated with the patient cohort includes image analytic features extracted from a set of perioperative images associated with the patient cohort and metrics related to the patient outcomes from the one or more therapeutic options 450
Provide decision support information for the surgical candidate to a client device based on the one or more predictions, wherein the decision support information includes a recommendation relating to the one or more therapeutic options for the surgical candidate

FIG. 4

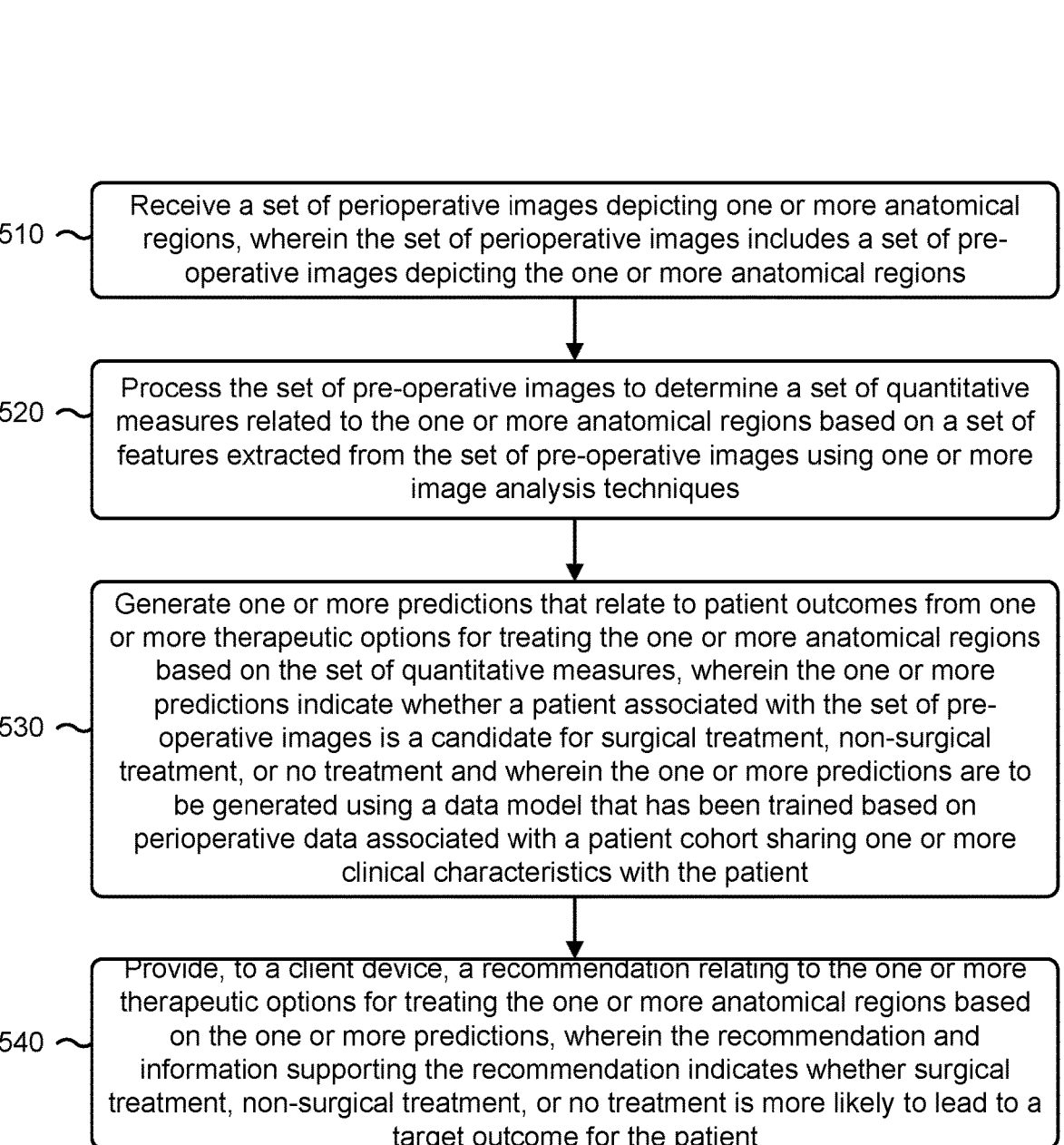

500

510 — Receive a set of perioperative images depicting one or more anatomical regions, wherein the set of perioperative images includes a set of pre-operative images depicting the one or more anatomical regions 520 — Process the set of pre-operative images to determine a set of quantitative measures related to the one or more anatomical regions based on a set of features extracted from the set of pre-operative images using one or more image analysis techniques 530 — Generate one or more predictions that relate to patient outcomes from one or more therapeutic options for treating the one or more anatomical regions based on the set of quantitative measures, wherein the one or more predictions indicate whether a patient associated with the set of pre-operative images is a candidate for surgical treatment, non-surgical treatment, or no treatment and wherein the one or more predictions are to be generated using a data model that has been trained based on perioperative data associated with a patient cohort sharing one or more clinical characteristics with the patient 540 — Provide, to a client device, a recommendation relating to the one or more therapeutic options for treating the one or more anatomical regions based on the one or more predictions, wherein the recommendation and information supporting the recommendation indicates whether surgical treatment, non-surgical treatment, or no treatment is more likely to lead to a target outcome for the patient

FIG. 5

600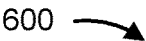

610 — Receive a set of images depicting one or more structures in an anatomical region of a patient 620 — Perform an image processing technique on the set of images to extract a set of features from the set of images and to determine a set of quantitative measures related to the one or more structures in the anatomical region of the patient based on the set of features 630 — Generate one or more predictions that relate to patient outcomes from one or more therapeutic options for the patient based on the set of quantitative measures, wherein the one or more predictions are to be generated using a data model that has been trained based on perioperative data associated with a patient cohort sharing one or more clinical characteristics with the patient, and wherein the perioperative data associated with the patient cohort includes image analytic features extracted from a set of perioperative images associated with the patient cohort and metrics related to the patient outcomes from the one or more therapeutic options 640 — Provide, to a client device, decision support information relating to the one or more therapeutic options for the patient based on the one or more predictions

FIG. 6

DATA ANALYTICS FOR PREDICTIVE MODELING OF SURGICAL OUTCOMES

RELATED APPLICATION(S)

This application is a 371 national stage of PCT Application PCT/US2020/019946 filed on Feb. 26, 2020, entitled "DATA ANALYTICS FOR PREDICTIVE MODELING OF SURGICAL OUTCOMES," which claims priority to U.S. Provisional Patent Application No. 62/812,691, filed on Mar. 1, 2019, the content of which is incorporated by reference herein in its entirety.

BACKGROUND

Clinical decision support systems are health information technology systems that are generally designed to provide a patient and/or health professionals (e.g., physicians, nurses, clinicians, staff, and/or the like) with relevant information to help inform decisions regarding the patient's care. For example, as the volume of data available to healthcare providers increases, clinicians cannot be reasonably expected to always have the ability to integrate all the available data into decision-making processes in an effective, reliable, and patient-specific manner. Such patient-specific decision-making and identification of suitable treatment pathways are important considering that multiple therapeutic modalities may be available and patients may have heterogeneous responses to different therapeutic modalities. Accordingly, clinical decision support systems are often designed to intelligently select and/or analyze the available healthcare data to suggest next steps for treatments, alert healthcare providers to available information that may not have been otherwise considered, identify potential risk-factors (e.g., medication interactions), provide information and/or suggestions to the clinical team and the patient, and/or the like.

SUMMARY

According to some implementations, a method may include: receiving a set of perioperative images depicting one or more anatomical regions of a surgical candidate, wherein the set of perioperative images includes a set of pre-operative images depicting the one or more anatomical regions of the surgical candidate; processing the set of pre-operative images to determine a first set of quantitative measures related to one or more structures in the one or more anatomical regions of the surgical candidate, wherein processing the set of pre-operative images includes: extracting a set of features from the set of pre-operative images using one or more image analysis techniques; and analyzing the set of features extracted from the set of pre-operative images to determine the first set of quantitative measures; receiving a second set of quantitative measures related to a clinical profile associated with the surgical candidate; generating one or more predictions that relate to patient outcomes from one or more therapeutic options for the surgical candidate based on the first set of quantitative measures and the second set of quantitative measures, wherein the one or more predictions are generated using a data model that has been trained based on perioperative data associated with a patient cohort sharing one or more clinical characteristics with the surgical candidate, and wherein the perioperative data associated with the patient cohort includes image analytic features extracted from a set of perioperative images associated with the patient cohort and metrics related to the patient outcomes from the one or more therapeutic options; and providing decision support information for the surgical candidate to a client device based on the one or more predictions, wherein the decision support information includes a recommendation relating to the one or more therapeutic options for the surgical candidate.

According to some implementations, a device may include one or more memories; and one or more processors, communicatively coupled to the one or more memories, configured to: receive a set of perioperative images depicting one or more anatomical regions, wherein the set of perioperative images includes a set of pre-operative images depicting the one or more anatomical regions; process the set of pre-operative images to determine a set of quantitative measures related to the one or more anatomical regions based on a set of features extracted from the set of pre-operative images using one or more image analysis techniques; generate one or more predictions that relate to patient outcomes from one or more therapeutic options for treating the one or more anatomical regions based on the set of quantitative measures, wherein the one or more predictions indicate whether a patient associated with the set of pre-operative images is a candidate for surgical treatment, non-surgical treatment, or no treatment, and wherein the one or more predictions are to be generated using a data model that has been trained based on perioperative data associated with a patient cohort sharing one or more clinical characteristics with the patient; and provide, to a client device, a recommendation relating to the one or more therapeutic options for treating the one or more anatomical regions based on the one or more predictions, wherein the recommendation and information supporting the recommendation indicates whether surgical treatment, non-surgical treatment, or no treatment is more likely to lead to a target outcome for the patient.

According to some implementations, a non-transitory computer-readable medium may store one or more instructions. The one or more instructions, when executed by one or more processors of a device, may cause the one or more processors to: receive a set of images depicting one or more structures in an anatomical region of a patient; perform an image processing technique on the set of images to extract a set of features from the set of images and to determine a set of quantitative measures related to the one or more structures in the anatomical region of the patient based on the set of features; generate one or more predictions that relate to patient outcomes from one or more therapeutic options for the patient based on the set of quantitative measures, wherein the one or more predictions are to be generated using a data model that has been trained based on perioperative data associated with a patient cohort sharing one or more clinical characteristics with the patient, and wherein the perioperative data associated with the patient cohort includes image analytic features extracted from a set of perioperative images associated with the patient cohort and metrics related to the patient outcomes from the one or more therapeutic options; and provide, to a client device, decision support information relating to the one or more therapeutic options for the patient based on the one or more predictions.

BRIEF DESCRIPTION OF THE DRAWINGS

FIGS. 1A-1D are diagrams of one or more example implementations described herein.

FIGS. 4-6 are flow charts of example processes for predictive modeling of surgical outcomes using data analytics.

DETAILED DESCRIPTION

Figure 1A:
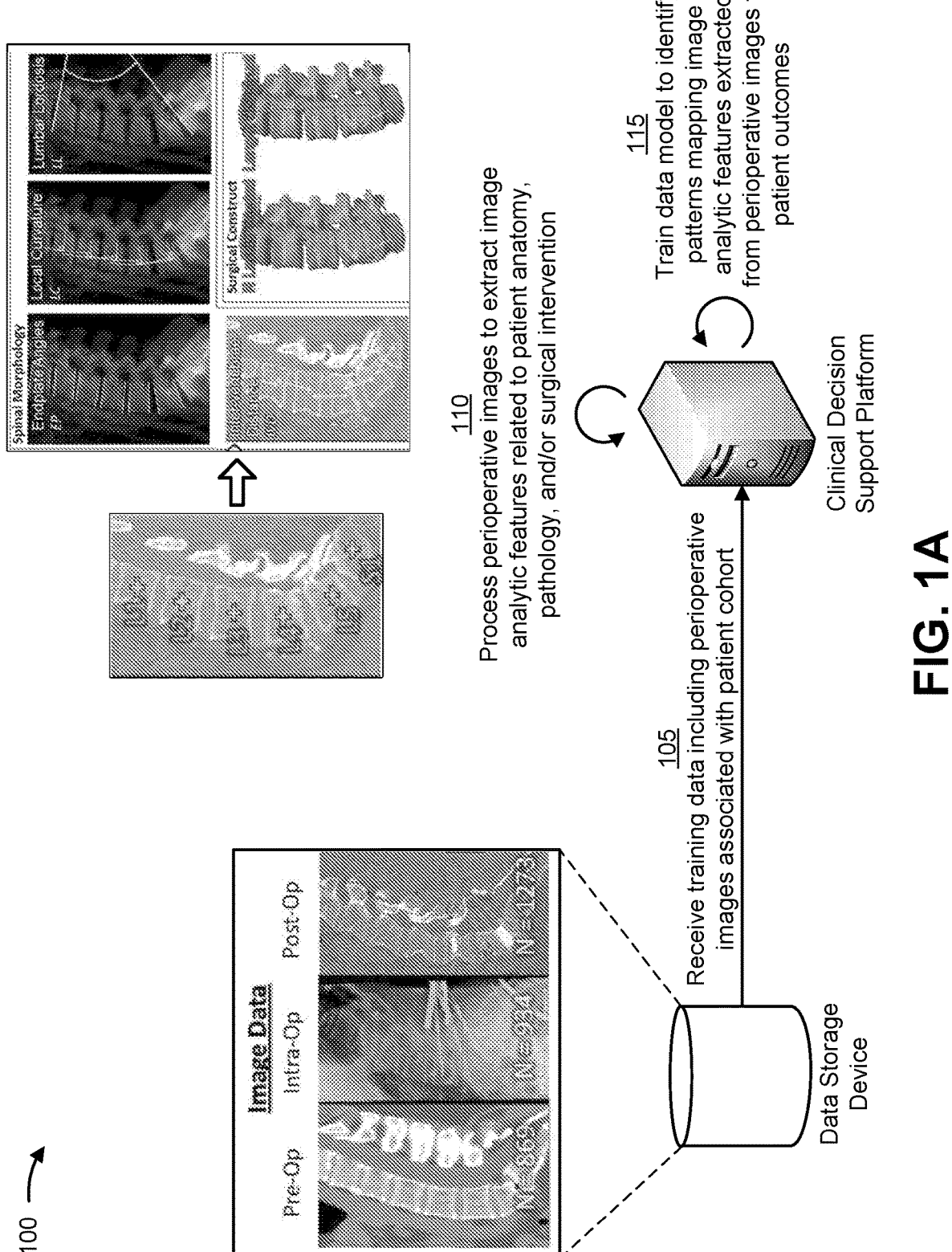

The following detailed description of example implementations refers to the accompanying drawings. The same reference numbers in different drawings may identify the same or similar elements.

There are many factors that may lead to uncertainty about how to approach care for a patient with a particular medical problem. For example, in the current landscape of spine surgery, there is a substantial variability in patient outcomes with undesired events such as revision surgery, failed back surgery, recurrent lumbar disc herniations, and/or the like becoming increasingly common. This variability in treating patients with common lumbar pathologies (e.g., low back pain, disc herniation, spondylolisthesis, and/or the like) may be attributable to a lack of evidence-based guidelines, as complex and multi-dimensional relationships between contributive factors and patient outcomes remain unclear and poorly understood. Furthermore, variations in patient outcomes may be caused by financial incentives (e.g., physicians recommending surgical treatment due to the substantially higher return relative to non-surgical treatment, insurance companies rejecting surgical treatment due to the high cost, and/or the like), different specialty and/or training backgrounds, variations in practice cultures between different geographical regions and practice settings (e.g., academic versus private practices), and/or the like. Accordingly, identifying patient cohorts (e.g., groups of patients sharing similar anatomy, symptoms, pathologies, and/or the like), determining the extent to which surgery may benefit a particular patient, and/or recommending patient-specific therapeutic options before, during, and/or after surgery, including options that do not involve surgery, remains a challenging task for patients, surgeons, other healthcare professionals, and/or the like.

Consequently, decision-making processes used to recommend surgical versus non-surgical options, select relevant surgical planning options (when surgical options are chosen), prognosticate a surgical outcome, and determine optimal rehabilitative options tends to suffer from uncertainty, variability, and subjectivity. For example, one approach aimed at understanding factors that determine outcome variability from spine surgery involves predictive modeling based on patient demographic and peri-operative clinical characteristics as potential predictors of outcome variability (e.g., age, sex, body mass index, smoking status, prior spinal surgery, pre-operative and/or post-operative pain intensity, and/or the like). Concomitantly, images are routinely acquired in the perioperative diagnostic and therapeutic pipeline, which as used herein refers to diagnostic and/or therapeutic phases that occur at any time before surgery, during surgery, and/or after surgery. These images generally include various features related to patient anatomy, pathology, changes effected during surgery, and/or the like. However, existing predictive models are limited to using patient demographic and/or clinical information (e.g., conventional information captured within a patient's medical record) without considering image-based information and/or limiting the use of image-based information to manually determined, qualitative characterization by a healthcare professional.

This may lead to undesirable medical outcomes for patients in addition to unnecessarily and/or inefficiently consuming resources used to plan and implement a treatment pathway for a patient. For example, when a surgical treatment is chosen for a patient who may benefit more or suffer less harm from an alternate surgical treatment or a non-surgical treatment (including no treatment or delayed treatment), the patient may be more likely to develop complications, need additional surgery or other treatment, and/or the like. Furthermore, patients do not uniformly benefit from a given surgical treatment plan, whereby existing predictive models that do not incorporate image-based information fall short in providing decision support information with respect to whether an individual patient should undergo surgery, the surgical plan to be followed if surgery is indicated, a rehabilitative plan to be followed, and/or the like. Furthermore, due to these drawbacks, various resources (e.g., healthcare resources, processing resources, memory resources, power resources, communication resources, and/or the like) associated with medical imaging devices, storage devices, devices used in planning treatment, and/or the like may be wasted when there is a need to remedy an undesired outcome such as revision surgery, failed surgery, recurrent injury, and/or the like. Furthermore, when a surgical treatment is chosen for a patient who may benefit equally or more from non-surgical treatment, this may waste resources (e.g., healthcare resources, processing sources, memory resources, power resources, communication resources, and/or the like) associated with devices used to plan the surgery, devices used to communicate with insurance provider systems, devices used to capture intra-operative and post-operative images, and/or the like.

Some implementations described herein may use data analytics for predictive modeling of surgical outcomes (e.g., outcomes from spinal surgery) based on perioperative images, perioperative data (e.g., demographic and/or clinical data), and/or the like. More particularly, as used herein, the term "perioperative" and variants thereof may refer to any time period or combination of time periods that occur before surgery (including cases where the patient does not undergo surgery), during surgery, and/or after surgery (e.g., immediately following surgery, during a follow-up visit, and/or the like). Accordingly, a clinical decision support platform may use the data analytics to assist in patient-specific surgical decision support, including selection of treatment course (e.g., operative or non-operative), surgical planning (e.g., selection of parameters affecting the surgical construct), prognostics on post-operative outcome, guiding a rehabilitative pathway based on the selected treatment course, and/or the like. For example, in some implementations, the clinical decision support platform may automatically derive image-based analytic features that can form a quantitative basis to predict a surgical outcome based on perioperative images (e.g., pre-operative (including cases where the patient does not undergo surgery), intra-operative, and/or post-operative images, which may include x-ray radiography and/or fluoroscopy images, computed tomography (CT) scans, magnetic resonance imaging (MRI) scans based on various pulse sequences and/or protocols, nuclear medicine images such as positron-emission tomography (PET) and/or single-photon emission computed tomography (SPECT) images, ultrasound images, optical images such as optical coherence tomography images, photography or videography capturing gait kinematics, contrast-enhanced variations on the above imaging techniques in which an extrinsic contrast agent is introduced into a patient, and/or the like). Furthermore, in some implementations, the quantitative basis to predict the surgical outcome may further include patient demographic and/or clinical characteristics (e.g., BMI, age, sex, smoking status, prior clinical and/or surgical history, and/or the like).

In some implementations, a data model used to predict surgical outcomes may incorporate one more machine learning or artificial intelligence techniques to identify statistical patterns, surgical characteristics, and/or other predictor variables among a patient cohort (e.g., a group of patients that have undergone a similar type of surgery) based on quantitative information related to patient anatomy, pathology, surgical intervention, and/or the like, which may be extracted from perioperative images associated with the patient cohort. For example, when used to predict outcomes from spine surgery, example features extracted from the perioperative images may include local and global spinal morphology, vertebral levels treated, instrumentation used, deviation of a surgical construct as-delivered relative to a planned delivery of the surgical construct, and/or the like. These and/or other image-based features may be input to the data model and used to compute a predicted outcome (e.g., pain and function characteristics). Used pre-operatively, the clinical decision support platform may use the predicted outcome to provide decision support information that can be considered in identifying patients more likely to benefit from surgical treatment versus non-surgical treatment, no treatment, delayed treatment, and/or the like, selecting optimal surgical and therapeutic approaches, and/or the like. Used post-operatively, the clinical decision support platform may use the predicted outcome in combination with features extracted from intra-operative images, features extracted from post-operative images, actual outcome data, and/or the like to evaluate the treatment plan that was selected for the patient, provide further decision support in guiding the post-operative (e.g., rehabilitative) pathway, update the data model, and/or the like.

In this way, the clinical decision support platform may mitigate use of resources associated with selecting and/or carrying out an appropriate patient-specific treatment plan. For example, when the data analytics are used to predict that a given patient would benefit equally or more from non-surgical treatment or no treatment, this may conserve resources (e.g., patient morbidity, healthcare resources, processing resources, memory resources, power resources, communication resources, financial resources, and/or the like) that would otherwise be wasted planning surgical treatment, capturing intra-operative and/or post-operative images, performing the surgical treatment, scheduling rehabilitation visits, and/or the like. Furthermore, even when a patient is predicted to benefit from surgical treatment, the data analytics can be used to determine optimal surgical constructs, enable early differentiation of post-operative recovery from abnormal outcomes necessitating further medical intervention, and/or the like. Accordingly, the data analytics used by the clinical decision support platform may conserve various computing resources (e.g., patient morbidity, healthcare resources, processing resources, memory resources, power resources, communication resources, and/or the like) in addition to leading to better health outcomes for patients, saving financial resources, and/or the like.

FIGS. 1A-1D are diagrams of one or more example implementations 100 described herein. As will be described in further detail herein, example implementation(s) 100 may include a clinical decision support platform, a data storage

Figure 1C:
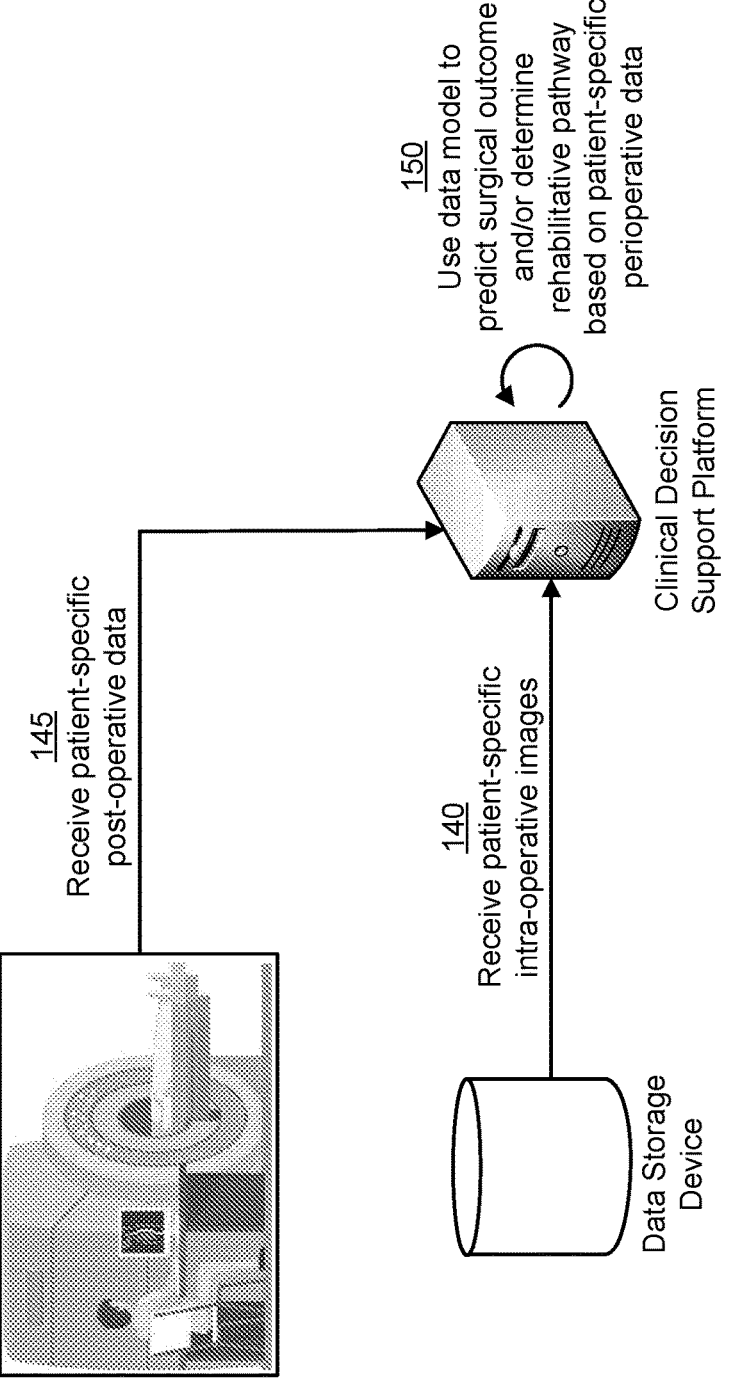
Figure 1D:
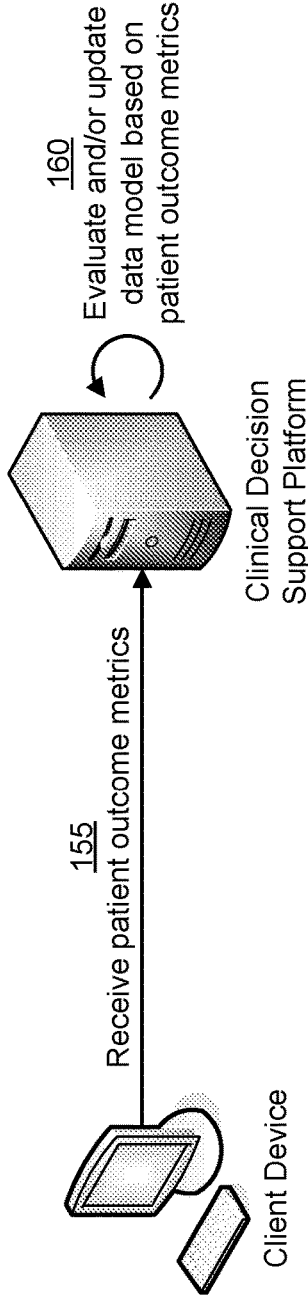

6 device, one or more medical imaging devices, and one or more client devices. As shown in FIG. 1A, the clinical decision support platform may train a data model to identify one or more patterns that map image analytic features extracted from perioperative images to patient outcomes based on perioperative data associated with a patient cohort (e.g., a group of patients sharing similar symptoms, undergoing similar treatment, and/or the like). As shown in FIG. 1B, the clinical decision support platform may use the trained data model to provide decision support information including one or more patient-specific therapeutic options based on image analytic features extracted from one or more patient-specific pre-operative images. As shown in FIG. 1C, when surgical treatment is selected for a given patient, the clinical decision support platform may use image analytic features extracted from one or more intra-operative and/or post-operative images to predict and/or evaluate a surgical outcome. As shown in FIG. 1D, the clinical decision support platform may evaluate and/or update the data model based on one or more metrics relating to an outcome for a patient who underwent a treatment plan based on the decision support information.

As shown in FIG. 1A, and by reference number 105, the clinical decision support platform may receive, from the data storage device, training data that includes perioperative images associated with a patient cohort, which generally includes a group of patients experiencing similar anatomy, symptoms, pathologies, and/or the like, which may be monitored over a period of time. For example, the patient cohort may include a group of patients that have undergone spinal surgery or were candidates for spinal surgery, and the perioperative images may include pre-operative images, intra-operative images, and/or post-operative images associated with the group of patients. Furthermore, as described herein, the perioperative images may include any suitable pre-operative, intra-operative, and/or post-operative images, such as x-ray radiography and/or fluoroscopy images, CT scans, MRI scans, nuclear medicine images such as PET and/or SPECT images, ultrasound images, optical images such as optical coherence tomography images, photography or videography, contrast-enhanced variations on the above imaging techniques, and/or the like.

Furthermore, in some implementations, the training data received from the data storage device may include clinical data, which may include demographic and/or clinical data associated with the patient cohort (e.g., age, sex, BMI, smoking status, diabetes status, hypertension status, bone pathologies, albumin levels, prior clinical history such as prior surgical status, and/or the like). In some implementations, the training data received from the data storage device may also include metrics related to treatment outcomes for the various patients in the patient cohort. For example, the metrics related to the treatment outcomes may indicate whether a given patient was subject to surgical or non-surgical treatment, and the metrics may further include quantitative measures related to patient pain and/or function after the relevant treatment (e.g., pain and/or function measures after three months, twelve months, and/or the like). In some implementations, the quantitative measures may be based on a Patient-Reported Outcomes Measurement Information System (PROMIS), a Short Form (36) Health Survey, a Nurick grading system, a modified Japanese Orthopedic Association (mJOA) scale, an Oswestry Disability Index (ODI), qualitative patient-reported outcomes (e.g., whether and/or when the patient is able to return to work, changes in activities that the patient is able to perform or unable to perform, and/or the like), and/or the like.

As further shown in FIG. 1A, and by reference number 110, the clinical decision support platform may process the perioperative images received from the data storage device to extract various image analytic features related to patient anatomy, pathology, surgical intervention, and/or the like. For example, in FIG. 1A, the perioperative images include pre-operative spinal images, intra-operative spinal images, and post-operative spinal images. Accordingly, in the illustrated example, the image analytic features extracted from the perioperative images may include various features such as those characterizing anatomy and morphology of the spine, surgical implants or other instrumentation, and/or the like.

In some implementations, to extract the anatomical and morphological spinal features from the perioperative images, the clinical decision support platform may employ a vertebra annotation algorithm to identify a centroid of each vertebra in the perioperative images (e.g., denoted by a '+' in FIG. 1A). The clinical decision support platform may use the vertebra centroids as inputs to one or more image analytic algorithms configured to derive features related to spine morphology. For example, in some implementations, the features related to spine morphology may include vertebral endplate angles (EP), local curvature (LC), lumbar lordosis (LL) based on a lateral digitally-reconstructed radiograph (DRR), an inter vertebrae distance (IVD), paraspinal soft-tissue, and/or the like. Furthermore, in some cases, the perioperative images may depict one or more medical devices implanted in a patient (e.g., pre-operative images may show surgical instrumentation implanted in the patient during a prior surgery, intra- and post-operative images may show actual or planned surgical instrumentation implanted in the patient during and after a planned surgery, and/or the like). For example, in the case of spinal surgery, the one or more medical devices may include a plate, a pedicle screw, an expandable cage, an artificial disc, a rod, a connector, an interspinous stabilization device, a vertebral body tethering, an interbody device, and/or the like. Accordingly, in some implementations, the image analytic features extracted from the perioperative images may quantify information related to the one or more medical devices (e.g., a number of vertebral levels treated, a length of a surgical construct, and/or the like), which may be derived by automatically segmenting surgical instrumentation from the perioperative images.

In some implementations, the image analytic features extracted from the perioperative images may additionally, or alternatively, include features derived from automatic surgical planning algorithms that compute an optimal placement of surgical instrumentation within a surgical construct. For example, in some implementations, the perioperative images may include one or more images that are constructed to depict a planned surgical construct using machine learning techniques, artificial intelligence techniques, and/or the like (e.g., a deep network may be trained to construct a radiograph that depicts a planned surgical construct such that image analytic features can be extracted from the constructed image(s)). Accordingly, in some implementations, the image analytic features may quantify a deviation of a surgical construct as-delivered relative to the optimal surgical construct computed by the automatic surgical planning algorithm. Additionally, or alternatively, the image analytic features extracted from the perioperative images may quantify one or more pathologies depicted in the perioperative images (e.g., bone mineral density, image texture within inter-vertebra space, image features of fused vertebra, and/or the like).

As further shown in FIG. 1A, and by reference number 115, the clinical decision support platform may train a data model to identify one or more patterns mapping the image analytic features extracted from the perioperative images to the metrics that relate to patient outcomes. In some implementations, the data model may be trained to identify the one or more patterns based on patient demographic and/or clinical data in combination with the image analytic features.

For example, the clinical decision support platform may obtain the image analytic features extracted from the perioperative images associated with the patient cohort, the demographic and/or clinical data associated with the patient cohort, data related to treatments for the patient cohort (e.g., surgical or non-surgical treatment, surgical instrumentation in cases of surgical treatment, and/or the like), and metrics related to outcomes from the treatments for the patient cohort (hereinafter collectively be referred to as "perioperative data") to generate and/or train the data model. In some implementations, the clinical decision support platform may process the perioperative data to train the data model to predict, for one or more sets of quantitative measures that include measures related to image analytics extracted from perioperative images, an outcome from a given treatment option.

More particularly, in some implementations, the clinical decision support platform may perform a set of data manipulation procedures to process the perioperative data to generate the data model, such as a data pre-processing procedure, a model training procedure, a model verification procedure, and/or the like. For example, the clinical decision support platform may pre-process the perioperative data to remove irrelevant information, confidential data, corrupt data, and/or the like. In this way, the clinical decision support platform may organize thousands, millions, or billions of data points for machine learning and model generation.

In some implementations, as mentioned above, the clinical decision support platform may perform a training operation when generating the data model. For example, the clinical decision support platform may portion the perioperative data into a training set (e.g., a set of data to train the model), a validation set (e.g., a set of data used to evaluate a fit of the model and/or to fine tune the model), a test set (e.g., a set of data used to evaluate a final fit of the model), and/or the like. In some implementations, a minimum feature set may be created from pre-processing and/or dimensionality reduction of the perioperative data. In some implementations, the clinical decision support platform may train the data model on this minimum feature set, thereby reducing processing required to train the data model, and may apply a classification technique to the minimum feature set.

In some implementations, the clinical decision support platform may use a classification technique, such as a Boosted Decision Tree classification technique, a logistic regression classification technique, a random forest classification technique, a gradient boosting machine (GBM) classifier technique, and/or the like to determine a categorical outcome (e.g., that particular perioperative data is associated with a particular outcome score relating to pain and/or function). Additionally, or alternatively, the clinical decision support platform may perform a recursive feature elimination procedure to split the data of the minimum feature set into partitions and/or branches, and use the partitions and/or branches to perform predictions (e.g., that particular perioperative data is associated with a particular outcome score relating to pain and/or function). Based on using the recursive feature elimination procedure, the clinical decision support platform may reduce utilization of computing resources relative to manual, linear sorting and analysis of data points, thereby enabling use of thousands, millions, or billions of data points to train the data model, which may result in a more accurate data model than using fewer data points.

Additionally, or alternatively, the clinical decision support platform may use a support vector machine (SVM) technique to generate a non-linear boundary between data points in the training set. In this case, the non-linear boundary is used to classify test data (e.g., perioperative data) into a particular class (e.g., a class indicating that particular perioperative data is associated with a particular outcome score relating to pain and/or function) or regress to an outcome score.

Additionally, or alternatively, the clinical decision support platform may train the data model using a supervised training procedure that includes receiving input to the model from a subject matter expert, which may reduce an amount of time, an amount of processing resources, and/or the like to train the data model relative to an unsupervised training procedure. In some implementations, the clinical decision support platform may use one or more other model training techniques, such as deep learning, a neural network technique, a latent semantic indexing technique, probabilistic graphical models, and/or the like. For example, the clinical decision support platform may perform an artificial neural network processing technique (e.g., using a two-layer feedforward neural network architecture, a three-layer feedforward neural network architecture, deeper networks and architectures, and/or the like) to perform pattern recognition with regard to patterns of particular perioperative data associated with particular outcome scores (e.g., outcome scores relating to pain, function, and/or the like). In this case, using the artificial neural network processing technique may improve an accuracy of the data model generated by the clinical decision support platform by being more robust to noisy, imprecise, or incomplete data, and by enabling the clinical decision support platform to detect patterns and/or trends undetectable to human analysts or systems using less complex techniques. Furthermore, in some implementations, the data model may be used to identify one or more image features that are most important in forming a patient-specific prediction. For example, a set of features relating to spinal curvature may be most important in informing decision-making for one patient, while a set of features relating to paraspinal muscle, fat, and BMI may be most important in informing decision-making for another patient. In this regard, the data model may be an "interpretable" data model (e.g., a boosted decision tree) that facilitates identifying which feature or set of features are most important. Additionally, or alternatively, the data model may include a "black box" data model (e.g., a deep learning model) that may generally produce accurate predictions but require other techniques to interpret or otherwise determine which feature(s) may be driving the decision-making.

In some implementations, a different device, such as a server device, may generate and train the data model. The different device may send the data model for use by the clinical decision support platform. The different device may update and send (e.g., on a scheduled basis, on an on-demand basis, on a triggered basis, on a periodic basis, and/or the like) the data model to the clinical decision support platform.

Accordingly, the clinical decision support platform may use artificial intelligence techniques, machine learning techniques, deep learning techniques, and/or the like to determine an association between certain perioperative data (e.g., quantitative measures related to image analytic features extracted from perioperative images, quantitative measures related to patient demographics, and/or the like), therapeutic options, and predicted patient outcomes (e.g., outcome classes, outcome scores, and/or the like).

As shown in FIG. 1B, and by reference number 120, the clinical decision support platform may receive a set of patient-specific pre-operative images from a medical imaging device. For example, the set of patient-specific pre-operative images may include one or more x-ray radiography and/or fluoroscopy images, CT scans, MRI scans, nuclear medicine images such as PET and/or SPECT images, ultrasound images, optical images such as optical coherence tomography images, photography or videography, contrast-enhanced variations on the above imaging techniques, and/or the like. As further shown in FIG. 1B, and by reference number 125, the clinical decision support platform may extract, from the set of pre-operative images, one or more patient-specific image analytic features.

For example, when the set of patient-specific pre-operative images are associated with a patient who is a potential candidate for spinal surgery, the set of pre-operative images may be processed to extract a set of quantitative measures that relate to a spinal morphology of the patient. In such cases, the clinical decision support platform may employ the vertebra annotation algorithm to identify a centroid of each vertebra in the set of pre-operative images, and the vertebra centroids may be used as inputs to derive the quantitative measures that relate to the spinal morphology of the patient (e.g., a vertebral endplate angle (EP), a local curvature (LC), a lumbar lordosis (LL), an inter-vertebrae distance (IVD), paraspinal soft-tissue, and/or the like). Furthermore, in cases where the pre-operative images depict one or more medical devices implanted in the patient (e.g., from a prior surgery), the patient-specific image analytic features may quantify information related to the one or more medical devices (e.g., a number of vertebral levels treated, a length of a surgical construct, and/or the like). Additionally, or alternatively, the quantitative measures extracted from the set of pre-operative images may relate to one or more pathologies depicted in the set of pre-operative images (e.g., bone mineral density, image texture within inter-vertebra space, image features of fused vertebra, and/or the like).

As further shown in FIG. 1B, and by reference number 130, the clinical decision support platform may use the data model to determine one or more recommendations related to a therapeutic pathway and/or to select one or more surgical parameters based on the image analytic features extracted from the patient-specific pre-operative images. In some implementations, the clinical decision support platform may determine the one or more recommendations related to the therapeutic pathway and/or select the one or more surgical parameters based further on one or more quantitative measures based on a profile including clinical data and/or demographic data associated with the patient.

For example, in some implementations, the clinical decision support platform may input the quantitative measures extracted from the set of pre-operative images, the quantitative measures based on the profile associated with the patient, and/or the like into the data model, which may output one or more scores that relate to a predicted outcome for certain therapeutic options (e.g., based on the patterns identified in the perioperative data associated with the patient cohort sharing one or more symptomatic characteristics with the patient). In some implementations, the one or more scores may be used to predict whether the patient would benefit more from surgical treatment, non-surgical treatment, delayed treatment, no treatment, and/or the like. Furthermore, when the patient would benefit more from surgical treatment, the one or more scores may be used to predict outcomes (e.g., in terms of pain and/or function) based on various surgical parameters (e.g., a number of levels to treat, a length of a surgical construct, and/or the like).

Accordingly, as shown in FIG. 1B, and by reference number 135, the clinical decision support platform may provide, to a client device, decision support information that includes certain patient-specific therapeutic options. For example, the client device may be associated with the patient, a healthcare provider (e.g., a physician, a nurse, and/or the like), an insurance company, and/or another party involved in healthcare decision-making for the patient. In some implementations, the decision support information may include one or more recommendations regarding which therapeutic option(s) are likely to lead to the best outcome for the patient (e.g., surgical treatment, non-surgical treatment, no treatment, and/or the like), and in some implementations, the decision support information may further include one or more recommendations regarding specific parameters associated with the recommended therapeutic option(s) (e.g., surgical parameters, non-surgical rehabilitation plans, and/or the like based on perioperative data associated with other patients sharing similar clinical characteristics as the patient). In some implementations, the client device may be configured to present the decision support information using one or more user interfaces. For example, in some implementations, the one or more user interfaces may present information related to one or more therapeutic options most likely to lead to a target outcome for the patient, information supporting the recommendations and/or specific parameters associated with the recommended therapeutic option(s) (e.g., perioperative images, demographic data, clinical data, and/or other information that may form a basis for the decision support information), and/or the like. In some implementations, the one or more user interfaces may include interactive elements to allow a user to explore different therapeutic options, simulate parameter changes, and/or the like.

As shown in FIG. 1C, and by reference number 140, the clinical decision support platform may receive one or more patient-specific intra-operative images from the data storage device. For example, the one or more patient-specific intra-operative images may be captured during a surgical treatment to guide the surgical procedure, to ensure that the intended operation is safely and correctly executed, and/or the like. Furthermore, as shown in FIG. 1C, and by reference number 145, the clinical decision support platform may receive patient-specific post-operative data. For example, the patient-specific post-operative data may include one or more patient-specific post-operative images that are captured after a surgical treatment (e.g., immediately afterwards, during a follow-up visit, and/or the like) to assess surgical instrumentation that may have been implanted in the patient during the surgical treatment, to evaluate how the patient's spinal morphology responded to the surgical treatment, and/or the like. Accordingly, when surgical treatment is selected for a given patient, the clinical decision support platform may use the intra-operative images and/or post-operative images to extract further image analytic features to evaluate the surgical procedure, the patient's recovery, and/ or the like. Additionally, or alternatively, the patient-specific post-operative data may include health and/or activity data obtained from one or more wearable devices or other patient-facing electronic devices. In some implementations, the health and/or activity data obtained from the wearable devices may include any suitable health and/or activity information that may be relevant to a treatment plan that was selected for a given patient regardless of whether the treatment plan includes surgical treatment, non-surgical treatment, no treatment, delayed treatment, and/or the like. For example, in some implementations, the health and/or activity data may include information related to heartrate, blood pressure, respiration rate, blood oxygen saturation, blood glucose, skin perspiration, capnography, body temperature, motion evaluation, posture monitoring, ambient parameters, status of implanted surgical instrumentation (if any), and/or the like. Accordingly, in some implementations, regardless of the particular treatment plan that is selected for a patient (e.g., surgical, non-surgical, or no treatment), the clinical decision support platform may use the health and/or activity data obtained from the one or more wearable devices to further evaluate the treatment plan that was selected for the patient.

As further shown in FIG. 1C, and by reference number 150, the clinical decision support platform may use the data model to predict an outcome from the surgical treatment and/or determine an optimal rehabilitative pathway for the patient based on patient-specific perioperative data, which may include image analytic features extracted from perioperative images associated with the patient (e.g., pre-operative, intra-operative, and post-operative images), health and/ or activity data obtained from one or more wearable devices, demographic and/or clinical data, and/or the like. For example, in some implementations, the image analytic features extracted from the perioperative images may be derived from one or more surgical planning algorithms that can compute an optimal placement of surgical instrumentation within a surgical construct, and the clinical decision support platform may determine (e.g., based on intra-operative and/or post-operative images) a deviation of the surgical construct as-delivered relative to the optimal placement computed by the surgical planning algorithm(s). In another example, to predict the outcome, the clinical decision support platform may compare image analytic features extracted from pre-operative images to image analytic features extracted from intra-operative and/or post-operative features to evaluate whether the spinal morphology of the patient is showing improvement following the surgical treatment. In other examples, the clinical decision support platform may use the image analytic features extracted from the perioperative images to predict pain and/or function levels at one or more future points in time (e.g., at a three-month follow-up visit, a twelve-month follow-up visit, and/or the like), to differentiate expected post-operative recovery from abnormal outcomes that may merit further medical intervention, and/or the like. In still another example, the clinical decision support platform may compare health and/or activity data obtained from the one or more wearable devices during a pre-operative or treatment planning phase to health and/or activity data obtained from the one or more wearable devices during follow-up visits to evaluate the treatment plan.

As shown in FIG. 1D, and by reference number 155, the clinical decision support platform may receive one or more patient outcome metrics from a client device. For example, in some implementations, the patient outcome metrics may comprise quantitative measures based on a Patient-Reported Outcomes Measurement Information System (PROMIS), a Short Form (36) Health Survey, a Nurick grading system, a modified Japanese Orthopedic Association (mJOA) scale, an Oswestry Disability Index (ODI), and/or the like. In some implementations, the patient outcome metrics may be gathered at one or more follow-up visits after a surgical treatment, at one or more visits during an ongoing non-surgical therapy, and/or the like. Furthermore, in some implementations, the patient outcome metrics may include health and/or activity data obtained from one or more wearable devices or other patient-facing electronic devices, as described above. Additionally, or alternatively, the patient outcome metrics may include one or more qualitative patient-reported outcomes (e.g., whether and/or when the patient was able to return to work, changes in activities that the patient is able to perform or unable to perform, and/or the like).

As further shown in FIG. 1D, and by reference number 160, the clinical decision support platform may evaluate and/or update the data model based on the one or more patient outcome metrics. For example, where a deviation between the patient outcome metrics for a given patient and the outcome that was predicted for that patient satisfies a threshold value, the data model may be updated to take the deviation into account such that the mapping between a given set of image analytic features, demographic data points, and/or clinical data points associated with the patient and predicted outcomes for certain therapeutic options are updated accordingly. Additionally, or alternatively, where the patient outcome metrics are within a threshold value of the outcome that was predicted for that patient, the data model may be updated to reinforce the mapping between a given set of image analytic features, demographic data points, and/or clinical data points associated with the patient, the therapeutic option that was chosen for the patient, and the predicted outcome for the patient. Accordingly, the clinical decision support platform may evaluate and/or update the data model such that subsequent predictions based on a given set of image analytic features, demographic data points, clinical data points, and/or the like are more likely to lead to a beneficial patient outcome.

As indicated above, FIGS. 1A-1D are provided merely as one or more examples. Other examples may differ from what is described with regard to FIGS. 1A-1D. For example, implementations have been described herein in a context that relates to the clinical decision support platform using perioperative image analytics to generate decision support information, predict patient outcomes, and/or the like with respect to spinal surgery. However, it will be appreciated that implementations described herein may be used to generate decision support information, predict patient outcomes, and/or the like with respect to other medical interventions that use perioperative medical images (e.g., orthopedic surgery, neurosurgery, ear, nose, and throat (ENT) surgery (otolaryngology—head and neck surgery), interventional radiology, ophthalmology, surgical oncology, and/or the like).

Figure 2:
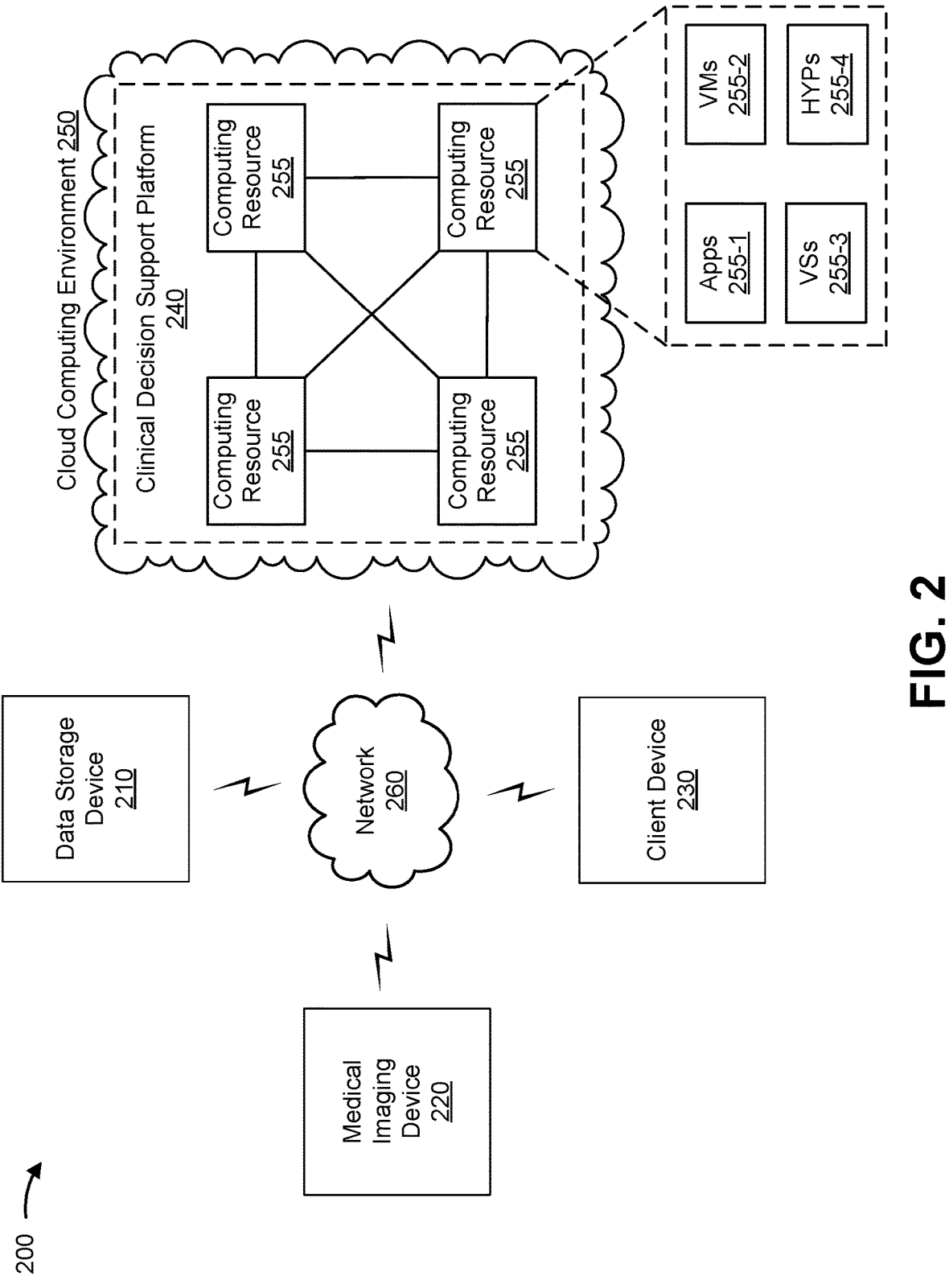
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a data storage device 210, a medical imaging device 220, a client device 230, a clinical decision support platform 240 in a cloud computing environment 250 that includes one or more computing resources 255, a network 260, and/or the like. Devices of environment 200 may interconnect via wired connections, wireless connections, or a combination of wired and wireless connections.

Data storage device 210 includes one or more devices capable of receiving, generating, storing, processing, and/or providing information associated with perioperative images, demographic data, patient outcome metrics, and/or the like.

For example, in some implementations, data storage device 210 may include a server device, a hard disk device, an optical disk device, a solid-state drive (SSD), a compact disc (CD), a network attached storage (NAS) device, a Flash memory device, a cartridge, a magnetic tape, and/or another device that can store and provide access to perioperative images, demographic data, patient outcome metrics, and/or the like.

Medical imaging device 220 includes one or more devices capable of receiving, generating, storing, processing, and/or providing information associated with a set of perioperative images (e.g., pre-operative images, intra-operative images, and/or post-operative images). For example, medical imaging device 220 may include a magnetic resonance imaging (MRI) device, an X-ray device, a computed tomography (CT) scan device, a positron emission tomography (PET) device, an ultrasound imaging (USI) device, a photoacoustic imaging (PAI) device, an optical coherence tomography (OCT) device, an elastography imaging device, and/or a similar type of device. In some implementations, medical imaging device 220 may generate and provide one or more perioperative images to clinical decision support platform 240. For example, in some implementations, the one or more perioperative images may include x-ray radiography and/or fluoroscopy images, CT scans, MRI scans, nuclear medicine images such as PET and/or SPECT images, ultrasound images, optical images such as optical coherence tomography images, photography or videography, contrast-enhanced variations on the above imaging techniques, and/or the like.

Client device 230 includes one or more devices capable of receiving, generating, storing, processing, and/or providing information, such as information described herein. For example, client device 230 may include a computer (e.g., a desktop computer, a laptop computer, a tablet computer, a handheld computer, a workstation computer, a server device, and/or the like), a mobile phone (e.g., a smart phone, a radiotelephone, and/or the like), an internet of things (IoT) device or smart appliance, a wearable communication device (e.g., a smart wristwatch, a pair of smart eyeglasses, an activity monitoring device, a wearable medical device, an implanted or implantable medical device, and/or the like) or a similar device. In some implementations, client device 230 may transmit information (e.g., perioperative data associated with one or more patients) to clinical decision support platform 240, receive information (e.g., decision support information relating to one or more therapeutic options for a patient) from clinical decision support platform 240, and/or the like. In some implementations, client device 230 may be associated with a patient, a healthcare provider (e.g., a physician, nurse, clinician, and/or the like), an insurance company, and/or any other party involved in healthcare decision-making for the patient. In some implementations, as described above, client device 230 may be configured to present the decision support information using one or more user interfaces.

Clinical decision support platform 240 includes one or more devices capable of receiving, generating, storing, processing, and/or providing information associated with perioperative images, demographic data, patient outcome metrics, and/or the like. For example, based on a set of pre-operative images associated with a patient, clinical decision support platform 240 may predict an outcome from one or more therapeutic options for the patient using one or more data models that have been trained based on perioperative data associated with a patient cohort sharing one or more symptomatic characteristics with the patient. In some implementations, clinical decision support platform 240 may provide decision support information based on the predicted outcome to client device 230 to assist the patient, healthcare professionals, and/or the like in choosing a therapeutic pathway for the patient. In some implementations, clinical decision support platform 240 may receive intra-operative, post-operative, and/or other perioperative images for one or more patients and use the data model to evaluate the therapeutic pathway that was chosen for the one or more patients and/or update the data model accordingly (e.g., based on an actual outcome for the patient).

In some implementations, as shown, clinical decision support platform 240 may be hosted in a cloud computing environment 250. Notably, while implementations described herein describe clinical decision support platform 240 as being hosted in cloud computing environment 250, in some implementations, clinical decision support platform 240 may be non-cloud-based (e.g., may be implemented outside of a cloud computing environment) or partially cloud-based.

Cloud computing environment 250 includes an environment that hosts clinical decision support platform 240. Cloud computing environment 250 may provide computation, software, data access, storage, and/or other services that do not require end-user knowledge of a physical location and configuration of system(s) and/or device(s) that hosts clinical decision support platform 240. As shown, cloud computing environment 250 may include a group of computing resources 255 (referred to collectively as "computing resources 255" and individually as "computing resource 255").

Computing resource 255 includes one or more personal computers, workstation computers, server devices, or other types of computation and/or communication devices. In some implementations, computing resource 255 may host clinical decision support platform 240. The cloud resources may include compute instances executing in computing resource 255, storage devices provided in computing resource 255, data transfer devices provided by computing resource 255, and/or the like. In some implementations, computing resource 255 may communicate with other computing resources 255 via wired connections, wireless connections, or a combination of wired and wireless connections.

As further shown in FIG. 2, computing resource 255 includes a group of cloud resources, such as one or more applications ("APPs") 255-1, one or more virtual machines ("VMs") 255-2, virtualized storage ("VSs") 255-3, one or more hypervisors ("HYPs") 255-4, and/or the like.

Application 255-1 includes one or more software applications that may be provided to or accessed by client device 230. Application 255-1 may eliminate a need to install and execute the software applications on client device 230. For example, application 255-1 may include software associated with clinical decision support platform 240 and/or any other software capable of being provided via cloud computing environment 250. In some implementations, one application 255-1 may send/receive information to/from one or more other applications 255-1, via virtual machine 255-2.

Virtual machine 255-2 includes a software implementation of a machine (e.g., a computer) that executes programs like a physical machine. Virtual machine 255-2 may be either a system virtual machine or a process virtual machine, depending upon use and degree of correspondence to any real machine by virtual machine 255-2. A system virtual machine may provide a complete system platform that supports execution of a complete operating system ("OS"). A process virtual machine may execute a single program, and may support a single process. In some implementations, virtual machine 255-2 may execute on behalf of a user (e.g., a user of client device 230), and may manage infrastructure of cloud computing environment 250, such as data management, synchronization, or long-duration data transfers.

Virtualized storage 255-3 includes one or more storage systems and/or one or more devices that use virtualization techniques within the storage systems or devices of computing resource 255. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 255-4 may provide hardware virtualization techniques that allow multiple operating systems (e.g., "guest operating systems") to execute concurrently on a host computer, such as computing resource 255. Hypervisor 255-4 may present a virtual operating platform to the guest operating systems, and may manage the execution of the guest operating systems. Multiple instances of a variety of operating systems may share virtualized hardware resources.

Network 260 includes one or more wired and/or wireless networks. For example, network 260 may include a cellular network (e.g., a long-term evolution (LTE) network, a code division multiple access (CDMA) network, a 3G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the internet, a fiber optic-based network, a cloud computing network, a mesh network and/or the like, and/or a combination of these or other types of networks.

The number and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
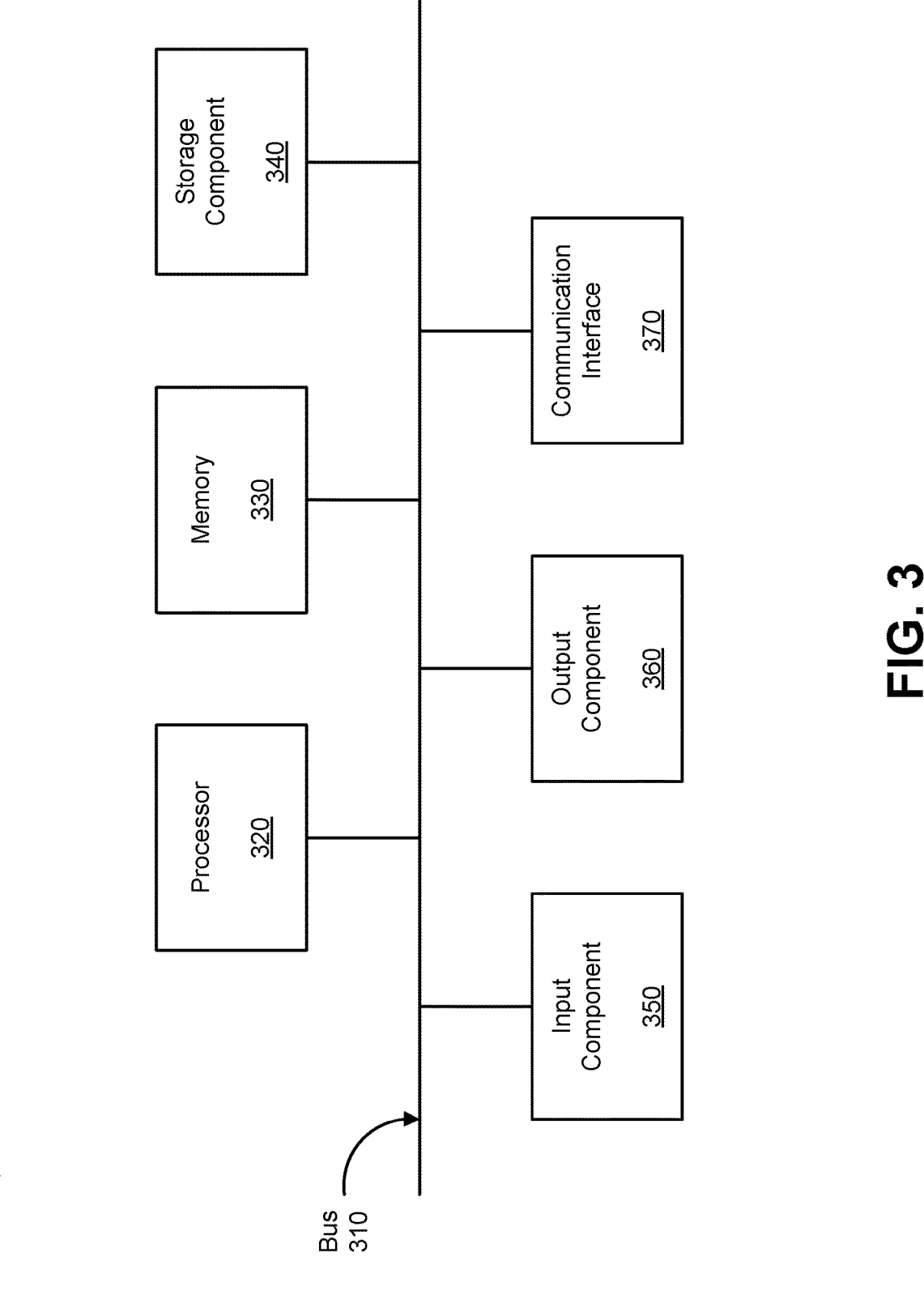
FIG. 3 is a diagram of example components of one or more devices of FIG. 2.

FIG. 3 is a diagram of example components of a device 300. Device 300 may correspond to data storage device 210, medical imaging device 220, client device 230, and/or clinical decision support platform 240. In some implementations, data storage device 210, medical imaging device 220, client device 230, and/or clinical decision support platform 240 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random-access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid-state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

FIG. 4 is a flow chart of an example process 400 for predictive modeling of surgical outcomes using image analytics. In some implementations, one or more process blocks of FIG. 4 may be performed by a clinical decision support platform (e.g., clinical decision support platform 240). In some implementations, one or more process blocks of FIG. 4 may be performed by another device or a group of devices separate from or including the clinical decision support platform, such as a data storage device (e.g., data storage device 210), a medical imaging device (e.g., medical imaging device 220), a client device (e.g., client device 230), and/or the like.

As shown in FIG. 4, process 400 may include receiving a set of perioperative images depicting one or more anatomical regions of a surgical candidate, wherein the set of perioperative images includes a set of pre-operative images depicting the one or more anatomical regions of the surgical candidate (block 410). For example, the clinical decision support platform may receive (e.g., using computing resource 255, processor 320, memory 330, storage component 340, input component 350, output component 360, communication interface 370, and/or the like) a set of perioperative images depicting one or more anatomical regions of a surgical candidate, as described above. In some implementations, the set of perioperative images includes a set of pre-operative images depicting the one or more anatomical regions of the surgical candidate.

As further shown in FIG. 4, process 400 may include processing the set of pre-operative images to determine a first set of quantitative measures related to one or more structures in the one or more anatomical regions of the surgical candidate (block 420). For example, the clinical decision support platform may process (e.g., using computing resource 255, processor 320, memory 330, storage component 340, input component 350, output component 360, communication interface 370, and/or the like) the set of pre-operative images to determine a first set of quantitative measures related to one or more structures in the one or more anatomical regions of the surgical candidate, as described above.

As further shown in FIG. 4, process 400 and block 420 may include extracting a set of features from the set of pre-operative images using one or more image analysis techniques (block 422). For example, the clinical decision support platform may extract (e.g., using processor 320, memory 330, storage component 340, input component 350, output component 360, communication interface 370, and/or the like) a set of features from the set of pre-operative images using one or more image analysis techniques, as described above.

As further shown in FIG. 4, process 400 and block 420 may include analyzing the set of features extracted from the set of pre-operative images to determine the first set of quantitative measures (block 424). For example, the clinical decision support platform may analyze (e.g., using computing resource 255, processor 320, memory 330, storage component 340, input component 350, output component 360, communication interface 370, and/or the like) the set of features extracted from the set of pre-operative images to determine the first set of quantitative measures, as described above.

As further shown in FIG. 4, process 400 may include receiving a second set of quantitative measures related to a clinical profile associated with the surgical candidate (block 430). For example, the clinical decision support platform may receive (e.g., using computing resource 255, processor 320, memory 330, storage component 340, input component 350, output component 360, communication interface 370, and/or the like) a second set of quantitative measures related to a clinical profile associated with the surgical candidate, as described above.

As further shown in FIG. 4, process 400 may include generating one or more predictions that relate to patient outcomes from one or more therapeutic options for the surgical candidate based on the first set of quantitative measures and the second set of quantitative measures, wherein the one or more predictions are generated using a data model that has been trained based on perioperative data associated with a patient cohort sharing one or more clinical characteristics with the surgical candidate, and wherein the perioperative data associated with the patient cohort includes image analytic features extracted from a set of perioperative images associated with the patient cohort and metrics related to the patient outcomes from the one or more therapeutic options (block 440). For example, the clinical decision support platform may generate (e.g., using computing resource 255, processor 320, memory 330, storage component 340, input component 350, output component 360, communication interface 370, and/or the like) one or more predictions that relate to patient outcomes from one or more therapeutic options for the surgical candidate based on the first set of quantitative measures and the second set of quantitative measures, as described above. In some implementations, the one or more predictions are generated using a data model that has been trained based on perioperative data associated with a patient cohort sharing one or more clinical characteristics with the surgical candidate. In some implementations, the perioperative data associated with the patient cohort includes image analytic features extracted from a set of perioperative images associated with the patient cohort and metrics related to the patient outcomes from the one or more therapeutic options.

As further shown in FIG. 4, process 400 may include providing decision support information for the surgical candidate to a client device based on the one or more predictions, wherein the decision support information includes a recommendation relating to the one or more therapeutic options for the surgical candidate (block 450). For example, the clinical decision support platform may provide (e.g., using computing resource 255, processor 320, memory 330, storage component 340, input component 350, output component 360, communication interface 370, and/or the like) decision support information for the surgical candidate to a client device based on the one or more predictions and wherein the decision support information includes a recommendation relating to the one or more therapeutic options for the surgical candidate, as described above. In some implementations, the decision support information includes a recommendation relating to the one or more therapeutic options for the surgical candidate.

Process 400 may include additional implementations, such as any single implementation or any combination of implementations described below and/or in connection with one or more other processes described elsewhere herein.

In a first implementation, the one or more therapeutic options include one or more of surgical treatment, non-surgical treatment, delayed treatment, or no treatment.

In a second implementation, alone or in combination with the first implementation, the one or more anatomical regions depicted in the set of perioperative images relate to a spinal morphology of the surgical candidate and the first set of quantitative measures include one or more of a vertebral endplate angle, a vertebra local curvature, a lumbar lordosis, or an inter-vertebrae distance.

In a third implementation, alone or in combination with one or more of the first and second implementations, the set of pre-operative images further depict one or more medical devices implanted in the surgical candidate and the first set of quantitative measures further include a quantity of vertebral levels treated by the one or more medical devices and a length of the one or more medical devices.

In a fourth implementation, alone or in combination with one or more of the first through third implementations, the second set of quantitative measures related to the clinical profile include one or more of an age, a sex, a body mass index, a smoking status, a diabetes status, a hypertension status, a bone pathology, an albumin level, or a prior spinal surgery status for the surgical candidate.

In a fifth implementation, alone or in combination with one or more of the first through fourth implementations, the second set of quantitative measures include one or more of health data or activity data obtained from one or more wearable devices.

In a sixth implementation, alone or in combination with one or more of the first through fifth implementations, the set of perioperative images further includes a set of intra-operative images depicting the one or more anatomical regions of the surgical candidate during a surgical treatment and a set of post-operative images depicting the one or more anatomical regions of the surgical candidate subsequent to the surgical treatment, and process 400 may further include processing the set of intra-operative images and the set of post-operative images to determine a third set of quantitative measures that relates to the one or more structures in the one or more anatomical regions of the surgical candidate, and generating an output evaluating an outcome from the surgical treatment based on a comparison of the first set of quantitative measures and the third set of quantitative measures.

In a seventh implementation, alone or in combination with one or more of the first through sixth implementations, the clinical decision support platform may receive one or more metrics relating to an outcome of the surgical treatment and update the data model based on the one or more metrics.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIG. 5 is a flow chart of an example process 500 for predictive modeling of surgical outcomes using image analytics. In some implementations, one or more process blocks of FIG. 5 may be performed by a clinical decision support platform (e.g., clinical decision support platform 240). In some implementations, one or more process blocks of FIG. 5 may be performed by another device or a group of devices separate from or including the clinical decision support platform, such as a data storage device (e.g., data storage device 210), a medical imaging device (e.g., medical imaging device 220), a client device (e.g., client device 230), and/or the like.

As shown in FIG. 5, process 500 may include receiving a set of perioperative images depicting one or more anatomical regions, wherein the set of perioperative images includes a set of pre-operative images depicting the one or more anatomical regions (block 510). For example, the clinical decision support platform may receive (e.g., using computing resource 255, processor 320, memory 330, storage component 340, input component 350, output component 360, communication interface 370, and/or the like) a set of perioperative images depicting one or more anatomical regions, as described above. In some implementations, the set of perioperative images includes a set of pre-operative images depicting the one or more anatomical regions.

As further shown in FIG. 5, process 500 may include processing the set of pre-operative images to determine a set of quantitative measures related to the one or more anatomical regions based on a set of features extracted from the set of pre-operative images using one or more image analysis techniques (block 520). For example, the clinical decision support platform may process (e.g., using computing resource 255, processor 320, memory 330, storage component 340, input component 350, output component 360, communication interface 370, and/or the like) the set of pre-operative images to determine a set of quantitative measures related to the one or more anatomical regions based on a set of features extracted from the set of pre-operative images using one or more image analysis techniques, as described above.

As further shown in FIG. 5, process 500 may include generating one or more predictions that relate to patient outcomes from one or more therapeutic options for treating the one or more anatomical regions based on the set of quantitative measures, wherein the one or more predictions indicate whether a patient associated with the set of pre-operative images is a candidate for surgical treatment, non-surgical treatment, or no treatment, and wherein the one or more predictions are to be generated using a data model that has been trained based on perioperative data associated with a patient cohort sharing one or more clinical characteristics with the patient (block 530). For example, the clinical decision support platform may generate (e.g., using computing resource 255, processor 320, memory 330, storage component 340, input component 350, output component 360, communication interface 370, and/or the like) one or more predictions that relate to patient outcomes from one or more therapeutic options for treating the one or more anatomical regions based on the set of quantitative measures, as described above. In some implementations, the one or more predictions indicate whether a patient associated with the set of pre-operative images is a candidate for surgical treatment, non-surgical treatment, or no treatment. In some implementations, the one or more predictions are to be generated using a data model that has been trained based on perioperative data associated with a patient cohort sharing one or more clinical characteristics with the patient.

As further shown in FIG. 5, process 500 may include providing, to a client device, a recommendation relating to the one or more therapeutic options for treating the one or more anatomical regions based on the one or more predictions, wherein the recommendation and information supporting the recommendation indicates whether surgical treatment, non-surgical treatment, or no treatment is more likely to lead to a target outcome for the patient (block 540). For example, the clinical decision support platform may provide (e.g., using computing resource 255, processor 320, memory 330, storage component 340, input component 350, output component 360, communication interface 370, and/or the like), to a client device, a recommendation relating to the one or more therapeutic options for treating the one or more anatomical regions based on the one or more predictions, as described above. In some implementations, the recommendation and information supporting the recommendation indicates whether surgical treatment, non-surgical treatment, or no treatment is more likely to lead to a target outcome for the patient.

Process 500 may include additional implementations, such as any single implementation or any combination of implementations described below and/or in connection with one or more other processes described elsewhere herein.

In a first implementation, the set of pre-operative images further depict one or more medical devices implanted in the patient and the set of quantitative measures relate to one or more of dimensions or a placement of the one or more medical devices within the patient.

In a second implementation, alone or in combination with the first implementation, the set of quantitative measures is a first set of quantitative measures, the set of perioperative images further includes a set of intra-operative images depicting the one or more anatomical regions of the patient during a surgical treatment and a set of post-operative images depicting the one or more anatomical regions of the patient subsequent to the surgical treatment, and process 500 further includes processing the set of intra-operative images and the set of post-operative images to determine a second set of quantitative measures that relates to the one or more anatomical regions of the patient, and generating an output evaluating an outcome from the surgical treatment based on a comparison of the first set of quantitative measures and the second set of quantitative measures.

In a third implementation, alone or in combination with one or more of the first and second implementations, the recommendation further indicates a plan for implanting a medical device in the patient based on the surgical treatment being more likely to lead to the target outcome, and the output indicates a deviation of the medical device implanted in the patient during the surgical treatment relative to a placement of the medical device indicated in the plan.

In a fourth implementation, alone or in combination with one or more of the first through third implementations, process 500 further includes receiving receive one or more metrics relating to an outcome of a treatment plan that was selected for the patient based on one or more of the recommendation or the information supporting the recommendation and updating the data model based on the one or more metrics.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

FIG. 6 is a flow chart of an example process 600 for predictive modeling of surgical outcomes using image analytics. In some implementations, one or more process blocks of FIG. 6 may be performed by a clinical decision support platform (e.g., clinical decision support platform 240). In some implementations, one or more process blocks of FIG. 6 may be performed by another device or a group of devices separate from or including the clinical decision support platform, such as a data storage device (e.g., data storage device 210), a medical imaging device (e.g., medical imaging device 220), a client device (e.g., client device 230), and/or the like.

As shown in FIG. 6, process 600 may include receiving a set of images depicting one or more structures in an anatomical region of a patient (block 610). For example, the clinical decision support platform may receive (e.g., using computing resource 255, processor 320, memory 330, storage component 340, input component 350, output component 360, communication interface 370, and/or the like) a set of images depicting one or more structures in an anatomical region of a patient, as described above.

As further shown in FIG. 6, process 600 may include performing an image processing technique on the set of images to extract a set of features from the set of images and to determine a set of quantitative measures related to the one or more structures in the anatomical region of the patient based on the set of features (block 620). For example, the clinical decision support platform may perform (e.g., using computing resource 255, processor 320, memory 330, storage component 340, input component 350, output component 360, communication interface 370, and/or the like) an image processing technique on the set of images to extract a set of features from the set of images and to determine a set of quantitative measures related to the one or more structures in the anatomical region of the patient based on the set of features, as described above.

As further shown in FIG. 6, process 600 may include generating one or more predictions that relate to patient outcomes from one or more therapeutic options for the patient based on the set of quantitative measures, wherein the one or more predictions are to be generated using a data model that has been trained based on perioperative data associated with a patient cohort sharing one or more clinical characteristics with the patient, and wherein the perioperative data associated with the patient cohort includes image analytic features extracted from a set of perioperative images associated with the patient cohort and metrics related to the patient outcomes from the one or more therapeutic options (block 630). For example, the clinical decision support platform may generate (e.g., using computing resource 255, processor 320, memory 330, storage component 340, input component 350, output component 360, communication interface 370, and/or the like) one or more predictions that relate to patient outcomes from one or more therapeutic options for the patient based on the set of quantitative measures, as described above. In some implementations, the one or more predictions are to be generated using a data model that has been trained based on perioperative data associated with a patient cohort sharing one or more clinical characteristics with the patient. In some implementations, the perioperative data associated with the patient cohort includes image analytic features extracted from a set of perioperative images associated with the patient cohort and metrics related to the patient outcomes from the one or more therapeutic options.

As further shown in FIG. 6, process 600 may include providing, to a client device, decision support information relating to the one or more therapeutic options for the patient based on the one or more predictions (block 640). For example, the clinical decision support platform may provide (e.g., using computing resource 255, processor 320, memory 330, storage component 340, input component 350, output component 360, communication interface 370, and/or the like), to a client device, decision support information relating to the one or more therapeutic options for the patient based on the one or more predictions, as described above.

Process 600 may include additional implementations, such as any single implementation or any combination of implementations described below and/or in connection with one or more other processes described elsewhere herein.

In a first implementation, the one or more therapeutic options include one or more of surgical treatment, non-surgical treatment, delayed treatment, or no treatment.

In a second implementation, alone or in combination with the first implementation, the one or more structures depicted in the set of images relate to a spinal morphology of the patient and the set of quantitative measures include one or more of a vertebral endplate angle, a vertebra local curvature, a lumbar lordosis, or an inter-vertebrae distance.

In a third implementation, alone or in combination with one or more of the first and second implementations, the set of quantitative measures is further related to one or more pathologies depicted in the set of images.

In a fourth implementation, alone or in combination with one or more of the first through third implementations, the one or more predictions that relate to the patient outcomes from the one or more therapeutic options are further based on a profile including one or more of demographic data, clinical data, or wearable device data associated with the patient.

In a fifth implementation, alone or in combination with one or more of the first through fourth implementations, the data model is a Boosted Decision Tree classifier.

In a sixth implementation, alone or in combination with one or more of the first through fifth implementations, the clinical decision support platform may identify a set of predictor variables based on the image analytic features extracted from the set of perioperative images associated with the patient cohort and train the data model to identify one or more statistical patterns mapping the set of predictor variables to the patient outcomes from the one or more therapeutic options.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, and/or the like). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:

receiving, at a device and from a medical imaging device, a set of perioperative images depicting one or more anatomical regions of a surgical candidate,
wherein the set of perioperative images depicting the one or more anatomical regions of the surgical candidate includes a set of pre-operative images depicting the one or more anatomical regions of the surgical candidate;

processing, by the device, the set of pre-operative images to determine a first set of quantitative measures related to one or more structures in the one or more anatomical regions of the surgical candidate, wherein processing the set of pre-operative images includes:

extracting a set of features from the set of pre-operative images using one or more image analysis techniques; and analyzing the set of features extracted from the set of pre-operative images to determine the first set of quantitative measures;

receiving, at the device, a second set of quantitative measures related to a clinical profile associated with the surgical candidate;

identifying, by the device and based on a data model that has been trained based on a minimum feature set created from at least one of pre-processing or dimensionality reduction of perioperative data associated with a patient cohort sharing one or more clinical characteristics with the surgical candidate, one or more image features that are to be used in forming one or more predictions that relate to patient outcomes from one or more therapeutic options for the surgical candidate, wherein the device further utilizes a recursive feature elimination procedure to split data of the minimum feature set into at least one or more partitions or branches, in order to reduce utilization of computing resources;

generating, by the device, the one or more predictions based on the first set of quantitative measures, the second set of quantitative measures, and based on the identified one or more image features, wherein the one or more predictions are generated using the data model, wherein the perioperative data associated with the patient cohort includes image analytic features extracted from a set of perioperative images associated with the patient cohort and metrics related to the patient outcomes from the one or more therapeutic options;

providing, by the device, decision support information for the surgical candidate to a client device based on the one or more predictions, wherein the decision support information includes a recommendation relating to the one or more therapeutic options for the surgical candidate;

updating, by the device, the data model based on one or more patient outcome metrics;

receiving a set of intra-operative data from a data storage device and a set of post-operative data obtained from a personal wearable electronic device of the surgical candidate, wherein the set of intra-operative data is captured during treatment of the one or more therapeutic options to ensure that an intended operation is executed properly and the set of intra-operative data is stored in the data storage device, and wherein the personal wearable electronic device of the surgical candidate obtains the set of post-operative data from the surgical candidate after the treatment of the one or more therapeutic options;

processing the set of intra-operative data and the post-operative data to determine a third set of quantitative measures;

generating, based on the data model, and based on comparing the first set of quantitative measures and the third set of quantitative measures, an output evaluating an outcome from the treatment of the one or more therapeutic options; and updating the data model to take a deviation value into account, when the deviation value satisfies a threshold value, or updating the data model to reinforce mapping between data associated with the data model, when the deviation value is within the threshold value, wherein the deviation value is related to deviation between patient outcome metrics and an outcome predicted for the patient.

2. The method of claim 1, wherein the one or more therapeutic options include one or more of surgical treatment, non-surgical treatment, delayed treatment, or no treatment.

3. The method of claim 1, wherein:

the one or more anatomical regions depicted in the set of perioperative images depicting the one or more anatomical regions of the surgical candidate relate to a spinal morphology of the surgical candidate, and the first set of quantitative measures include one or more of a vertebral endplate angle, a vertebra local curvature, a lumbar lordosis, or an inter-vertebrae distance.

4. The method of claim 3, wherein:

the set of pre-operative images further depict one or more medical devices implanted in the surgical candidate, and the first set of quantitative measures further include a quantity of vertebral levels treated by the one or more medical devices and a length of the one or more medical devices.

5. The method of claim 3, wherein the second set of quantitative measures related to the clinical profile include one or more of an age, a sex, a body mass index, a smoking status, a diabetes status, a hypertension status, a bone pathology, an albumin level, or a prior spinal surgery status for the surgical candidate.

6. The method of claim 1, wherein the second set of quantitative measures include one or more of health data or activity data obtained from one or more wearable devices including the personal wearable device.

7. The method of claim 1, further comprising:

receiving one or more metrics relating to an outcome of a surgical treatment; and updating the data model based on the one or more metrics.

8. The method of claim 1, wherein the set of post-operative data depicts the one or more anatomical regions of the surgical candidate after the treatment of the one or more therapeutic options.

9. A device, comprising:

one or more memories; and one or more processors, communicatively coupled to the one or more memories, configured to:

receive, from a medical imaging device, a set of perioperative images depicting one or more anatomical regions, wherein the set of perioperative images includes a set of pre-operative images depicting the one or more anatomical regions;

process the set of pre-operative images to determine a first set of quantitative measures related to the one or more anatomical regions based on a set of features extracted from the set of pre-operative images using one or more image analysis techniques;

identify, based on a data model that has been trained based on a minimum feature set created from at least one of pre-processing or dimensionality reduction of perioperative data associated with a patient cohort sharing one or more clinical characteristics with a patient, one or more image features that are to be used in forming one or more predictions that relate to patient outcomes from one or more therapeutic options for treating the one or more anatomical regions, wherein the device further utilizes a recursive feature elimination procedure to split data of the minimum feature set into at least one or more partitions or branches, in order to reduce utilization of computing resources;

generate the one or more predictions based on the first set of quantitative measures and based on the identified one or more image features, wherein the one or more predictions indicate whether the patient associated with the set of pre-operative images is a candidate for surgical treatment, non-surgical treatment, or no treatment, and wherein the one or more predictions are to be generated using the data model;

provide, to a client device, a recommendation relating to the one or more therapeutic options for treating the one or more anatomical regions based on the one or more predictions, wherein the recommendation and information supporting the recommendation indicates whether surgical treatment, non-surgical treatment, or no treatment is more likely to lead to a target outcome for the patient;

update the data model based on one or more patient outcome metrics;

receive a set of intra-operative data from a data storage device and a set of post-operative data obtained from a personal wearable electronic device of the candidate, wherein the set of intra-operative data is captured during treatment of the one or more therapeutic options to ensure that an intended operation is executed properly and the set of intra-operative data is stored in the data storage device, and wherein the personal wearable electronic device of the candidate obtains the set of post-operative data from the candidate after the treatment of the one or more therapeutic options;

process the set of intra-operative data and the post-operative data to determine a second set of quantitative measures;

generate, based on the data model, and based on comparing the first set of quantitative measure and the second set of quantitative measures, an output evaluating an outcome from the treatment of the one or more therapeutic options; and update the data model to take a deviation value into account, when the deviation value satisfies a threshold value, or update the data model to reinforce mapping between data associated with the data model, when the deviation value is within the threshold value, wherein the deviation value is related to deviation between patient outcome metrics and an outcome predicted for the patient.

10. The device of claim 9, wherein:

the set of pre-operative images further depict one or more medical devices implanted in the patient, and the first set of quantitative measures relate to one or more of dimensions or a placement of the one or more medical devices within the patient.

11. The device of claim 9, wherein:

the recommendation further indicates a plan for implanting a medical device in the patient based on the surgical treatment being more likely to lead to the target outcome, and the output indicates a deviation of the medical device implanted in the patient during the surgical treatment relative to a placement of the medical device indicated in the plan.

12. The device of claim 9, wherein the one or more processors are further configured to:

receive one or more metrics relating to an outcome of a treatment plan that was selected for the patient based on one or more of the recommendation or the information supporting the recommendation; and update the data model based on the one or more metrics.

13. The device of claim 9, wherein the set of post-operative data depicts the one or more anatomical regions of the candidate after the treatment of the one or more therapeutic options.

14. A non-transitory computer-readable medium storing instructions, the instructions comprising:

one or more instructions that, when executed by one or more processors, cause the one or more processors to:

receive, from a medical imaging device, a set of images depicting one or more structures in an anatomical region of a patient;

perform an image processing technique on the set of images to extract a set of features from the set of images and to determine a first set of quantitative measures related to the one or more structures in the anatomical region of the patient based on the set of features;

identify, based on a data model that has been trained based on a minimum feature set created from at least one of pre-processing or dimensionality reduction of perioperative data associated with a patient cohort sharing one or more clinical characteristics with the patient, one or more image features that are to be used in forming one or more predictions that relate to patient outcomes from one or more therapeutic options for the patient, wherein the device further utilizes a recursive feature elimination procedure to split data of the minimum feature set into at least one or more partitions or branches, in order to reduce utilization of computing resources;

generate the one or more predictions based on the first set of quantitative measures and based on the identified one or more image features, wherein the one or more predictions are to be generated using the data model, and wherein the perioperative data associated with the patient cohort includes image analytic features extracted from a set of perioperative images associated with the patient cohort and metrics related to the patient outcomes from the one or more therapeutic options;

provide, to a client device, decision support information relating to the one or more therapeutic options for the patient based on the one or more predictions;

update the data model based on one or more patient outcome metrics;

receive a set of intra-operative data from a data storage device and a set of post-operative data obtained from a personal wearable electronic device of the patient, wherein the set of intra-operative data is captured during treatment of the one or more therapeutic options to ensure that an intended operation is executed properly and the set of intra-operative data is stored in the data storage device, and wherein the personal wearable electronic device of the patient obtains the set of post-operative data from the patient after the treatment of the one or more therapeutic options;

process the set of intra-operative data and the post-operative data to determine a second set of quantitative measures;

generate, based on the data model, and based on comparing the first set of quantitative measures and the second set of quantitative measures, an output evaluating an outcome from the treatment of the one or more therapeutic options; and update the data model to take a deviation value into account, when the deviation value satisfies a threshold value, or updating the data model to reinforce mapping between data associated with the data model, when the deviation value is within the threshold value, wherein the deviation value is related to deviation between patient outcome metrics and an outcome predicted for the patient.

15. The non-transitory computer-readable medium of claim 14, wherein the one or more therapeutic options include one or more of surgical treatment, non-surgical treatment, delayed treatment, or no treatment.

16. The non-transitory computer-readable medium of claim 14, wherein:

the one or more structures depicted in the set of images relate to a spinal morphology of the patient, and the set of quantitative measures include one or more of a vertebral endplate angle, a vertebra local curvature, a lumbar lordosis, or an inter-vertebrae distance.

17. The non-transitory computer-readable medium of claim 14, wherein the first set of quantitative measures is further related to one or more pathologies depicted in the set of images.

18. The non-transitory computer-readable medium of claim 14, wherein the one or more predictions that relate to the patient outcomes from the one or more therapeutic options are further based on a profile including one or more of demographic data, clinical data, or wearable device data associated with the patient obtained from one or more wearable device including the persona wearable device.

19. The non-transitory computer-readable medium of claim 14, wherein the data model is a Boosted Decision Tree classifier.

20. The non-transitory computer-readable medium of claim 14, wherein the one or more instructions, when executed by the one or more processors, further cause the one or more processors to:

identify a set of predictor variables based on the image analytic features extracted from the set of perioperative images associated with the patient cohort; and train the data model to identify one or more statistical patterns mapping the set of predictor variables to the patient outcomes from the one or more therapeutic options.

* * * * *